United States Patent [19]

Kawaoka et al.

[11] 4,410,704
[45] Oct. 18, 1983

[54] N-SUBSTITUTED BENZOTHIAZOLE-2-SULFONAMIDES; METHOD OF THEIR PREPARATION; METHOD OF PREVENTING SCORCHING OF RUBBER

[75] Inventors: Yutaka Kawaoka; Hideo Oda; Masataka Yasumoto, all of Yanai; Kazuya Hirota; Yuji Ishinaga, both of Yamaguchi; Masakazu Morita, Yanai, all of Japan

[73] Assignee: Sanshin Kagaku Kogyo Co., Ltd., Yamaguchi, Japan

[21] Appl. No.: 254,544

[22] Filed: Apr. 15, 1981

[30] Foreign Application Priority Data

May 16, 1980 [JP] Japan ................................ 55-65040
May 16, 1980 [JP] Japan ................................ 55-65041
May 16, 1980 [JP] Japan ................................ 55-65042

[51] Int. Cl.³ .......................................... C07D 277/76
[52] U.S. Cl. ........................................ 548/166; 525/349
[58] Field of Search ............................ 548/166, 167

[56] References Cited

FOREIGN PATENT DOCUMENTS 2135543  1/1973  Fed. Rep. of Germany ...... 548/166
1288701  9/1972  United Kingdom ............... 548/167

Primary Examiner—Robert Gerstl
Attorney, Agent, or Firm—Sandler & Greenblum

[57] ABSTRACT

N-substituted benzothiazole-2-sulfonamide compounds represented by the general formula:

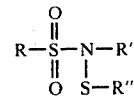

wherein R is selected from the group consisting of benzothiazolyl or substituted benzothiazolyl represented by the general formula:

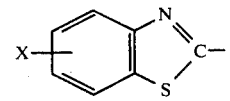

wherein X is selected from the group consisting of halogen, lower alkyl, lower alkoxy, acetamido or nitro;

R' is selected from the group consisting of hydrogen, alkyl, cycloalkyl, benzyl, phenyl, naphthyl, R"—S—, or substituted aryl represented by the general formula:

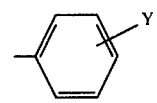

wherein Y is selected from the group consisting of halogen, lower alkyl, or nitro, or mixtures thereof; and R" being selected from the group consisting of alkyl, cycloalkyl, benzyl, phenyl, naphthyl, trichloromethyl or substituted aryl represented by the general formula:

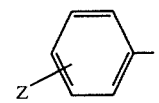

wherein Z is selected from the group consisting of halogen, lower alkyl, nitro or carboxy.

Methods of making and using the inventive compounds, including their use as scorch retardants.

3 Claims, 2 Drawing Figures

N-SUBSTITUTED BENZOTHIAZOLE-2-SULFONAMIDES; METHOD OF THEIR PREPARATION; METHOD OF PREVENTING SCORCHING OF RUBBER

BACKGROUND OF THE INVENTION

1. Field of the Invention

The invention relates to N-substituted benzothiazole-2-sulfonamide compounds of the general formula:

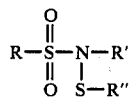

wherein R is benzothiazolyl or substituted benzothiazolyl represented by the general formula:

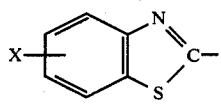

where X represents halogen, lower alkyl, alkoxy, acetamido or nitro;
R' is hydrogen, alkyl, cycloalkyl, benzyl, phenyl, naphthyl, R"—S—, or substituted aryl radical represented by the general formula:

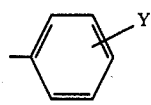

Y being halogen, lower alkyl, or nitro;
R" is alkyl, cycloalkyl, benzyl, trichloromethyl, phenyl, naphthyl, or substituted aryl represented by the general formula:

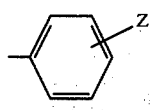

where Z represents halogen, lower alkyl, nitro or carboxy.

The invention further relates to a method of preparing the inventive compounds as well as to the use of these compounds as scorch retardants in rubbers and like materials.

2. Description of Prior Art

The N-substituted benzothiazole-2-sulfonamides of the invention strongly prevent prevulcanization of rubber compounds containing sulfur or sulfur donor curing agents and accelerators both in natural or diene synthetic rubbers.

In the rubber industry, it is very important to prevent scorching (or prevulcanization, burning, premature vulcanization) so as not to form scrap rubber and to make products with good physical properties.

The conventional method of preventing scorching in rubber compounds relies upon the use of a delayed action type accelerators such as benzothiazole-2-sulfenamides and further makes use of retardants such as phthalic anhydride or N-nitrosodiphenylamine.

These retardants are not satisfactory, because conventional organic acids reduce the effectiveness of sulfenamide accelerators by extending the time of vulcanization, and because the physical properties of the rubber products formed are not very good.

N-nitrosodiphenylamines become less effective when active carbon black is used, since carbon black absorbs N-nitrosodiphenylamines. By way of contrast, as a result of extensive screening tests of various kinds of organic compounds, we have found that the inventive N-substituted benzothiazole-2-sulfonamides are very effective for retarding prevulcanization when used in relatively small amounts compared with the conventional scorch retardants described above.

Halogen containing rubber compounds are cured by adding metal oxide, such as zinc oxide, substituted thiourea, polyamines or its derivatives, and recently, trithiocyanuric acid or 2-substituted-4,6-dimercapto-S-triazines.

Using these conventional vulcanization techniques, halogen containing rubber compounds are not only scorched, but also the vulcanization does not occur rapidly such that the end point of vulcanization is not sharply defined.

Besides the above mentioned retardants, some disulfides such as dibenzothiazyl disulfide (MBTS), tetramethylthiuram disulfide (TMTD) or N-cyclohexylbenzolthiazyl-2-sulfenamide (CBS) previously used as vulcanization accelerators for diene rubbers, have also been used as retardants, but in this case not only must large quantities be added; but the physical properties of the vulcanized rubber are inferior.

SUMMARY OF THE INVENTION

According to the invention, an N-substituted benzothiazole-2-sulfonamide is provided represented by the general formula:

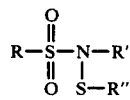

wherein R is selected from the group consisting of benzothiazolyl or substituted benzothiazolyl represented by the general formula:

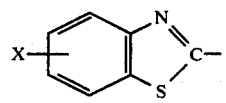

wherein X is selected from the group consisting of halogen, lower alkyl, lower alkoxy, acetamido or nitro;
R' is selected from the group consisting of hydrogen, alkyl, cycloalkyl, benzyl, phenyl, naphthyl, R"—S—, or substituted aryl represented by the general formula:

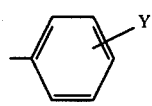

wherein Y is selected from the group consisting of halogen, lower alkyl, or nitro, or mixtures thereof; and R" being selected from the group consisting of alkyl, cycloalkyl, benzyl, phenyl, naphthyl, trichloromethyl or substituted aryl represented by the general formula:

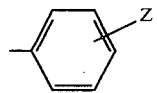

wherein Z is selected from the group consisting of halogen, lower alkyl, nitro or carboxy.

A method of preparing the above N-substituted benzothiazole-2-sulfonamide compounds is disclosed which comprises the step of reacting benzothiazole-2-sulfonamide represented by the formula:

$$R-\underset{\underset{O}{\|}}{\overset{\overset{O}{\|}}{S}}-\underset{H}{N}-R'$$

an alkali metal or ammonium salt thereof with a sulfenyl halide represented by the general formula:
R"—S—X' wherein X' is a halogen, in an inert solvent.

According to the invention, the above inventive compounds may be used to prevent scorching of natural or diene synthetic rubber, as well as of halogen containing rubbers by adding the inventive compounds to the rubber formulations prior to curing. Furthermore, scorched rubber may be recovered by adding the inventive compounds thereto.

BRIEF DESCRIPTION OF THE DRAWINGS

The invention will be described with reference to graphs shown in the figures.

DESCRIPTION OF PREFERRED EMBODIMENTS AND SPECIFIC EXAMPLES

Figure 1:
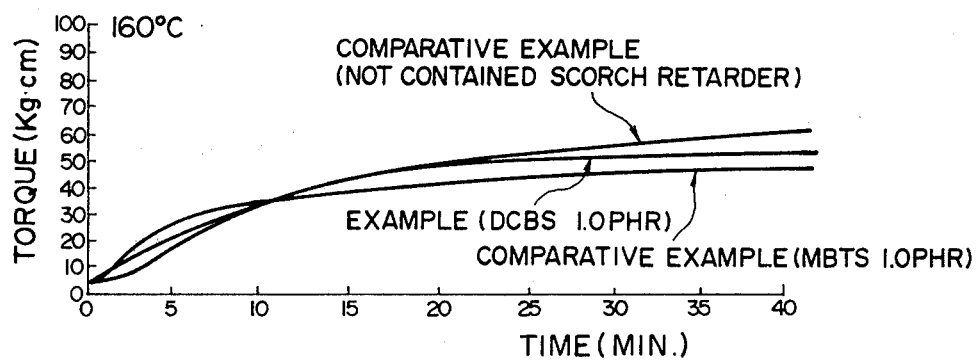
FIG. 1 illustrates bridging curves wherein DCBS (1.0 PHR) is compared with MBTS (1.0 PHR) and with a sample containing no scorch retardant.
Figure 2:
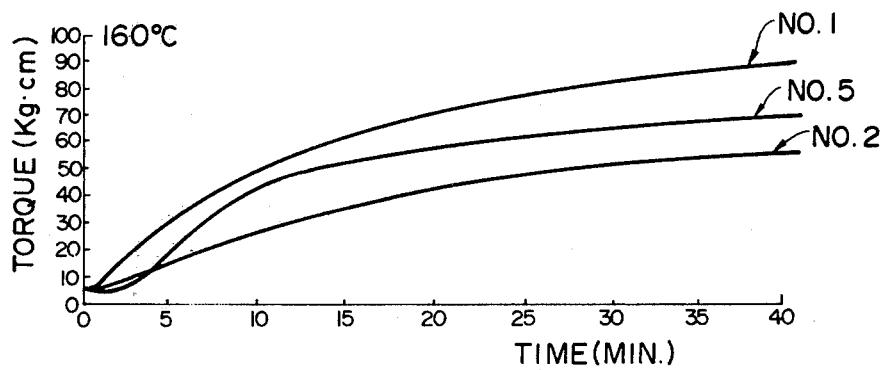
FIG. 2 illustrates the bridging curves corresponding to Examples 1, 2, and 5.

One important aim of this invention is to provide retardants which are efficient in small amounts while nevertheless forming vulcanized rubber having good physical properties.

In addition to their use as retardants, the inventive N-substituted benzothiazole-2-sulfonamides are also believed to be useful as stabilizers of rubber or plastics, medicines, agricultural chemicals, antimildew agents, antistaining agents for metals, lubricant additives, etc. and their intermediates.

The N-substituted benzothiazole-2-sulfonamides of the invention are generally described by the following general formula:

$$R-\underset{\underset{O}{\|}}{\overset{\overset{O}{\|}}{S}}-\underset{S-R''}{N}-R'$$

wherein R is benzothiazolyl or substituted benzothiazolyl represented by the general formula:

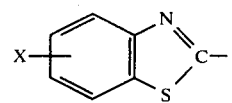

where X represents halogen, lower alkyl, alkoxy acetoamido or nitro; R' is hydrogen, alkyl, cycloalkyl, benzyl, phenyl, naphthyl, R"—S—, or substituted aryl radical represented by the general formula:

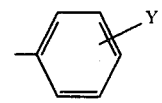

where Y is halogen, lower alkyl or nitro; R" is alkyl, cycloalkyl, benzyl, trichloromethyl, phenyl, naphthyl, or substituted aryl represented by the general formula:

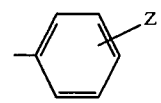

where Z is halogen, lower alkyl, nitro or carboxy.

PREPARATION

The inventive compounds may be synthesized by either of the following reactions:

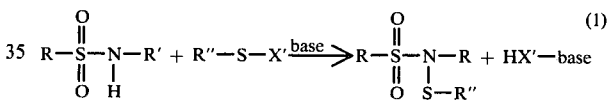

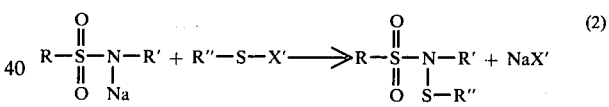

where R, R' and R" are the same as mentioned above and X' represents halogen.

Sulfenyl halides of the general formula R"—S—X can be obtained by the reaction of various mercaptans or their disulfides with halogen at low temperatures according to conventional techniques. In the above reactions, halogenated solvents such as anhydrous carbon tetrachloride, methylene chloride, trichloroethylene and perchloroethylene or hydrocarbon solvent such as n-pentane or n-hexane are used.

In reaction equation (1) tertiary amines such as triethanolamine or triethylamine are used as a hydrogen halide acceptor.

In the reaction shown in equations (1) and (2), the reactions can be carried out at any temperature, but relatively low temperatures on the order of about −10°∼50° C. are preferred.

In these reactions, any inert solvent, including halogentated solvents, such as dimethylformamide, carbon tetrachloride, trichloroethylene, perchloroethylene, methylene chloride, n-hexane, n-pentane, benzene, toluene, acetone, methanol and so on can be used.

Examples of compounds which may be synthesized according to the invention are: N-methylthio-N-cyclohexyl benzothiazole-2-sulfonamide, N-ethylthio-N-cyclohexyl benzothiazole-2-sulfonamide, N-n-propylthio-N-cyclohexyl benzothiazole-2-sulfonamide, N-isopropylthio-N-cyclohexyl benzothiazole-2-sulfonamide, N-n-butylthio-N-cyclohexyl benzothiazole-2-sulfonamide, N-sec-butylthio-N-cyclohexyl benzothiazole-2-sulfonamide, N-iso-butylthio-N-cyclohexyl benzothiazole-2-sulfonamide, N-t-butylthio-N-cyclohexyl benzothiazole-2-sulfonamide, N-n-amylthio-N-cyclohexyl benzothiazole-2-sulfonamide, N-n-hexylthio-N-cyclohexyl benzothiazole-2-sulfonamide, N-n-octylthio-N-cyclohexyl benzothiazole-2-sulfonamide, N-n-nonylthio-N-cyclohexyl benzothiazole-2-sulfonamide, N-n-dodecylthio-N-cyclohexyl benzothiazole-2-sulfonamide, N-t-dodecylthio-N-cyclohexyl benzothiazole-2-sulfonamide, N-cyclohexylthio-N-cyclohexyl benzothiazole-2-sulfonamide, N-phenylthio-N-cyclohexyl benzothiazole-2-sulfonamide, N-tolylthio-N-cyclohexyl benzothiazole-2-sulfonamide, N-nitrophenylthio-N-cyclohexyl benzothiazole-2-sulfonamide, N-chlorophenylthio-N-cyclohexyl benzothiazole-2-sulfonamide, N-2,4,5-trichlorophenylthio-N-cyclohexyl benzothiazole-2-sulfonamide, N-2-carboxyphenylthio-N-cyclohexyl benzothiazole-2-sulfonamide, N-benzylthio-N-cyclohexyl benzothiazole-2-sulfonamide, N-trichloromethylthio-N-cyclohexyl thiobenzothiazole-2-sulfonamide, N-naphthylthio-N-cyclohexyl benzothiazole-2-sulfonamide, N-cyclohexyl thiobenzothiazole-2-sulfonamide, N-cyclohexylthio-N-methyl benzothiazole-2-sulfonamide, N-cyclohexylthio-N-ethyl benzothiazole-2-sulfonamide, N-cyclohexylthio-N-n-propyl benzothiazole-2-sulfonamide, N-cyclohexylthio-N-n-butyl benzothiazole-2-sulfonamide, N-cyclohexylthio-N-t-butyl benzothiazole-2-sulfonamide, N-cyclohexylthio-N-phenyl benzothiazole-2-sulfonamide, N-cyclohexylthio-N-benzyl benzothiazole-2-sulfonamide, N-n-dodecylthio-N-chlorophenyl benzothiazole-2-sulfonamide, N-n-dodecylthio-N-nitrophenyl benzothiazole-2-sulfonamide, N-n-dodecylthio-N-naphthyl benzothiazole-2-sulfonamide, N-cyclohexylthio-N-cyclohexyl-5-chlorobenzothiazole-2-sulfonamide, N-cyclohexyl thio-N-cyclohexyl-5-methyl benzothiazole-2-sulfonamide, N-n-dodecylthio-N-cyclohexyl-5-methoxy benzothiazole-2-sulfonamide, N-n-octylthio-N-cyclohexyl-5-ethoxy benzothiazole-2-sulfonamide, N-n-butylthio-N-cyclohexyl-6-acetoamidobenzothiazole-2-sulfonamide, N-n-propylthio-N-cyclohexyl-nitrobenzothiazole-2-sulfonamide, N,N-dicyclohexylthio-benzothiazole-2-sulfonamide.

Methods of preparing N-substituted benzothiazole-2-sulfonamides according to the invention are illustrated with reference to the examples below:

EXAMPLE 1

Synthesis of N-n-octylthio-N-cyclohexyl benzothiazole-2-sulfonamide:

9.75 grams of chlorine (0.137 mole) is introduced into 70 ml of a stirred solution of 40 grams n-octylmercaptan (0.274 mole) in carbon tetrachloride and cooled at a temperature of about $-5°$ to $5°$ C. for about 15 minutes. Hydrogen chloride is purged with nitrogen gas, and 9.75 grams of chlorine (0.137 mole) is introduced during 15 minutes. The temperature of the reaction is kept between about $-5°$ and $5°$ C.

The resulting orange-red n-octyl chlorosulfide solution is added dropwise to a stirred solution of 77.5 grams of N-cyclohexyl benzothiazole-2-sulfonamide (0.26 mole) and 28 grams triethylamine (0.28 mole) in 300 ml anhydrous dimethylformamide at about $13°-17°$ C. over 80 minutes. After 90 minutes of stirring, the reaction mixture is poured into 2 liters of ice water. A muddy solid is obtained upon decanting the water. The solid is washed in 200 ml n-hexane and filtered by suction. 105 grams of light brownish white crystal is obtained.

When crystallized from a benzene-methanol mixture, the white crystals melt at about $80°-81°$ C. Analysis of the product indicates 56.99% carbon, 7.43% hydrogen, 6.37% nitrogen and 21.39% sulfur, compared to 57.27% carbon, 7.27% hydrogen, 6.36% nitrogen and 21.82% sulfur corresponding to $C_{21}H_{32}N_2S_3O_2$.

EXAMPLE 2

The synthesis of N-n-dodecylthio-N-cyclohexyl benzothiazole-2-sulfonamide:

58.5 grams (0.247 mole) of n-dodecyl chlorosulfide prepared as in Example 1 is added over a 70-minute period to a stirred solution containing 70 grams of N-cyclohexyl benzothiazole-2-sulfonamide (0.236 mole), and 25 grams of triethylamine (0.247 mole) in 200 ml anhydrous dimethylformamide. The temperature is maintained between about $10°$ and $15°$ C.

The reaction mixture is poured into 2 liters of ice water. A muddy solid is obtained by decanting the water. The product is washed in 200 ml of n-hexane and filtered by suction. 100 grams of light brownish-white crystal is obtained. The resulting crystals are recrystallized from a benzene-methanol solution. The recrystallized white crystal melt at about $77°-78°$ C. Analysis of the product indicates 60.27% carbon, 8.24% hydrogen, 5.60% nitrogen and 19.06% sulfur which, when compared to 60.48% carbon, 8.06% hydrogen, 5.65% nitrogen and 19.35% sulfur, corresponds to $C_{25}H_{40}N_2S_3O_2$.

EXAMPLE 3

Synthesis of N-cyclohexylthio-N-cyclohexyl benzothiazole-2-sulfonamide (No. 1):

38.9 grams of cyclohexyl chlorosulfide (0.258 mole) prepared as in Example 1 is added over a 50-minute period to a stirred solution containing 73 grams (0.247 mole) N-cyclohexyl benzothiazole-2-sulfonamide, 26 grams triethylamine (0.257 mole) in 300 ml anhydrous dimethylformamide. The temperature is maintained between about $12°$ and $16°$ C. After further stirring for 90 minutes, the reaction mixture is poured into 2.5 liters of ice water. Muddy solid is obtained as above. The product is washed in about 300 ml of n-hexane and is filtered by suction. 81 grams of light brownish white crystalline substance is obtained. The crystalline material recovered is recrystallized from benzene-methanol. The white crystal melts at about $134.5°-136°$ C.

Analysis of the product indicates 54.9% carbon, 6.30% hydrogen, 6.76% nitrogen and 23.28% sulfur, compared to 55.61% carbon, 6.34% hydrogen, 6.83% nitrogen and 23.41% sulfur corresponding to $C_{19}H_{26}N_2S_3O_2$.

EXAMPLE 4

Synthesis of N-cyclohexylthio-N-cyclohexyl benzothiazole-2-sulfonamide (No. 2):

6 grams of 48% sodium hydroxide solution is added to 30 ml methanol which is dehydrated with anhydrous sodium sulfate. 19.5 grams (0.0658 mole) of N-cyclohexyl benzothiazole-2-sulfonamide is dissolved in the above solution.

10.4 grams of cyclohexyl chlorosulfide (0.069 mole) prepared as in Example 1 is added over a 20-minute period to the above stirred solution to form the sodium salt of N-cyclohexyl benzothiazole-2-sulfonamide in methanol solution. The temperature is maintained at about 0°-5° C. After stirring for 60 minutes, the reaction product is filtered off, and well washed with n-hexane and water. After drying at about 40°-50° C., 21.5 grams of light grayish-white crystal is obtained. When recrystallized from benzene-methanol, the white crystals melt at about 135°-137.5° C. It is confirmed that the mixed melting point is depressed. The infrared ray absorption spectrum is the same as in Example 3.

EXAMPLE 5

Synthesis of N-cyclohexylthio-N-ethyl benzothiazole-2-sulfonamide:

7.8 grams (0.0517 mole) of cyclohexyl chlorosulfide prepared as in Example 1 is added over a 60-minute period to a stirred solution of 12 grams (0.0495 mole) of N-ethyl benzothiazole-2-sulfonamide, 5.5 grams of triethylamine (0.0495 mole) in 200 ml anhydrous dimethylformamide and 200 ml chloroform. The temperature is maintained between about 15° and 20° C. The reaction mixture is poured into 2 liters of ice water. The solvent layer is well washed, dehydrated with anhydrous sodium sulfate and any remaining solvent is removed by vacuum distillation.

A light brownish-white residue is obtained and the recovered crystals are recrystallized from a benzene-methanol solution.

The white crystalline substance (3.6 grams) melts at about 90°-93.5° C.

EXAMPLE 6

Synthesis of N-cyclohexylthio-N-cyclohexyl-5-chlorobenzothiazole-2-sulfonamide:

2.6 grams of cyclohexyl chlorosulfide (0.0172 mole) prepared as in Example 1 is added slowly to a stirred solution containing 5.4 grams (0.0163 mole) of N-cyclohexyl-5-chlorobenzothiazole-2-sulfonamide, and 2 grams of triethylamine (0.0178 mole) in 150 ml anhydrous dimethylformamide. The temperature is maintained between about 15° and 20° C. After stirring, 100 ml of chloroform is added and the reaction mixture is poured into 2 liters of ice water, and treated as in Example 5.

A white crystalline substance having a melting point of about 136.5°-139° C. is obtained.

EXAMPLES 7A-7F

Additional compounds of the invention have been prepared using synthesis techniques analogous to those described above, with the following results:

N-n-butylthio-N-cyclohexyl benzothiazole-2-sulfonamide; white crystals; m.p. about 97.5°-100° C.

N-n-hexylthio-N-cyclohexyl benzothiazole-2-sulfonamide; white crystals; m.p. about 77.5°-79° C.

N-phenylthio-N-cyclohexyl benzothiazole-2-sulfonamide; white crystals; m.p. about 105.5°-111° C.

N-P-tolylthio-N-cyclohexyl benzothiazole-2-sulfonamide; white crystals; m.p. about 134.5°-141.5° C.

N-cyclohexylthio-N-phenyl benzothiazole-2-sulfonamide; white crystals; m.p. about 123.5°-125° C. Analysis (calculated for $C_{19}H_{20}N_2S_3O_2$: 56.44% C; 4.95% H; 6.93% N; 23.76% S) found: 55.79% C; 4.86% H; 7.0% N; 23.1% S.

N-cyclohexylthio-N-cyclohexyl-5-chloro-benzothiazole-2-sulfonamide; white crystals; m.p. about 136.5°-139° C.

METHOD OF USE

The quantity of the inventive retardants used according to this invention for retarding scorching should preferably be about 0.1 to 5.0 parts by weight and particularly about 0.1 to 3.0 parts by weight of the rubber. The inventive retardants may be used in materials such as natural rubber, SBR, NBR, polybutadiene rubber (BR), polyisoprene rubber (IR), ethylenepropylene rubber (EPR), ethylenepropylene terpolymer (EP), mixtures and blends of these rubbers, and the halogenated derivatives of these rubbers.

By adding one or more compounds selected from N-substituted benzothiazole-2-sulfonamides in this invention to halogen containing rubbers, scorching is extremely reduced compared with conventional retardants. Halogen containing rubbers which may be cured according to this invention include: polychloroprene, polyepichlorohydrin rubber, epichlorohydrin-ethylene oxide copolymerized rubber, epichlorohydrin-propyleneoxide copolymerized rubber, chlorinated butyl rubber, chlorinated polyethylene, ethtylacrylate-chloroethylvinylether copolymerized rubber, fluorinated rubbers, and the like.

To protect against prevulcanization of halogen containing rubbers, one or more compounds selected from N-substituted benzothiazole-2-sulfonamides is added together with with conventional compounding ingredients such as vulcanization accelerators, activators, reinforcing agents, fillers, softerners, plasticizers, antioxidants and the like. As for curing agents, metallic oxides such as zinc oxide or magnesium oxide, and Group II, III or IV oxides may be used.

As was noted previously, a substantial difference between N-substituted benzothiazole-2-sulfonamides of the invention and conventional scorch retardants is that the inventive compounds prevent scorching when used in very small amounts. Additionally, scorch time and cure time can be controlled as desired by regulating the amount of the compound added; and scorched rubber can be reclaimed by adding the compounds of the invention.

For purposes of this invention, the term "sulfur vulcanization agent" is taken to mean elemental sulfur or sulfur containing vulcanizing agents, e.g., morpholine disulfide, thiuram disulfide, or thiuram polysulfide.

The compounds and process of the invention are applicable for use with accelerators of various classes. For example, thiazoles such as 2-mercaptobenzothiazole or dibenzothiazyl disulfide; sulfenamides such as N-cyclohexyl benzothiazole-2-sulfenamide; N-t-butyl benzothiazole-2-sulfenamide; N-oxydiethylene benzothiazole-2-sulfenamide; thiurams such as tetramethylthiuram disulfide, tetramethylthiuram monosulfide; dithiocarbamates such as the zinc salt of dimethyldithiocarbamate or the zinc salt of diethyldithiocarbamate; guanidines such as diphenylguanidine or di-o-tolylguanidine; aldehydeamines; and mixtures thereof.

The inventive process and compounds may be used in conjunction with various vulcanization accelerators, including thioura derivatives such as ethylene thiourea (2-mercaptoimidazoline), diethyl thiourea, trimethyl thiourea, fatty amines such as ethylenediamine, hexamethylene diamine, diethylene triamine; polyamine carbamates such as ethylenediamine carbamate, hexamethylene diamine carbamate; 2-substituted-4,6-dimercapto-S-triazines such as trithiocyanuric acid, 2-dimethylamino-4,6-dimercapto-S-triazine, 2-dibutylamino- 4,6-dimercapto-S-triazine, or 2-anilino-4,6-dimercapto-S-triazine; thiazine derivatives such as tetrahydro-3,5-dimethyl 2H-1,3,5-thiazine-2-thione, tetrahydro-3,5-diethyl 2H-1,3,5-thiazine-2-thione, tetrahydro-3,5-dibutyl 2H-1,3,5-thiazine-2-thione and 2-mercapto-1,3,4-thiadiazole. It should be clearly understood that the vulcanizing agents and vulcanization accelerators listed are merely exemplary and are by no means exhaustive.

Examples of the antiscorching effects of N-substituted benzothiazole-2-sulfonamide according to the invention are ilustrated below.

EXAMPLE 8

The compounds shown in Table 1 are mixed together by test rollers of 6.0"×12" at 50°±5° C. and the antiscorching effects and influence on rate of cure of the compounds of the invention are tested according to JIS 6300 (1974). Results of the Mooney scorch test at 120° C. are shown in Table 2, $V_m$ being minimum viscosity, $t_5$ being 5 point rise (min.), $t_{35}$ being 35 point rise (min.), and $t_{\Delta 30}$ being $t_{35}-t_5$.

Results of the curelastometer test at 140° C. and 150° C. are shown in Table 3. Results of the cure test are shown in table 4. The conditions of the curelastometer test are as follows:

Test instrument: JSR type curelastometer; dies: 2 mm; amplitude: ±3°; induction period: $t_{10}$ (min, sec); cure time: $t_{90}$ (min, sec); cure rate: R (min, sec); estimated cure time: $T=2\ t_{90}-t_{10}$ (min, sec).

TABLE 1

| RECIPE | |
|---|---|
| Natural Rubber | 100 parts by Wt |
| Zinc Oxide | 5 |
| Sulfur | 2.5 |
| Stearic Acid | 1 |
| Process Oil | 5 |
| Carbon Black (HAF) | 50 |
| Accelerator CBS* | 0.7 |
| Scorch Retarder | 1.0 or 0.5 |

*N—Cyclohexyl benzothiazole-2-sulfenamide

TABLE 2

| Scorch Retardant | PHR | $V_m$ | $t_5$ | $t_{35}$ | $t_{\Delta 30}$ |
|---|---|---|---|---|---|
| None | — | 33.0 | 18'00" | 20'30" | 2'30" |
| N—n-butylthio-N—cyclohexyl benzothiazole-2-sulfonamide | 0.5 | 26.0 | 30'50" | 32'50" | 2'00" |
|  | 1.0 | 25.0 | 36'00" | 38'10" | 2'10" |
| N—n-hexylthio-N—cyclohexyl benzothiazole-2-sulfonamide | 0.5 | 25.0 | 30'00" | 32'10" | 2'10" |
|  | 1.0 | 22.0 | 37'40" | 40'00" | 2'20" |
| N—n-octylthio-N—cyclohexyl benzothiazole-2-sulfonamide | 0.5 | 29.0 | 31'25" | 33'30" | 2'05" |
|  | 1.0 | 29.0 | 39'20" | 41'20" | 2'00" |
| N—n-dodecylthio-N—cyclohexyl benzothiazole-2-sulfonamide | 0.5 | 33.0 | 31'20" | 33'00" | 1'40" |
|  | 1.0 | 31.0 | 38'25" | 40'35" | 2'10" |
| N—phenylthio-N—cyclohexyl benzothiazole-2-sulfonamide | 0.5 | 27.0 | 29'00" | 31'10" | 2'10" |
|  | 1.0 | 27.0 | 37'55" | 40'00" | 2'05" |
| N—p-tolylthio-N—cyclohexyl benzothiazole-2-sulfonamide | 0.5 | 29.0 | 29'00" | 31'20" | 2'10" |
|  | 1.0 | 29.0 | 39'55" | 42'05" | 2'10" |
| N—cyclohexylthio-N—cyclohexyl benzothiazole-2-sulfonamide | 0.5 | 31.0 | 37'25" | 39'55" | 2'30" |
|  | 1.0 | 29.0 | 52'45" | 55'55" | 3'10" |
| N—cyclohexylthio-N—ethyl benzothiazole-2-sulfonamide | 1.0 | 31.0 | 53'05" | 56'20" | 3'15" |
| N—cyclohexylthio-N—phenyl benzothiazole-2-sulfonamide | 0.5 | 29.0 | 23'30" | 25'30" | 2'00" |
| N—cyclohexylthio-N—cyclohexyl-5-chlorobenzothiazole-2-sulfonamide | 1.0 | 36.0 | 53'50" | 58'05" | 4'15" |
| Phthalic anhydride (for comparison) | 0.5 | 28.0 | 24'30" | 26'55" | 2'25" |
|  | 1.0 | 31.0 | 29'10" | 32'55" | 3'45" |
| N—nitrosodiphenylamine (for comparison) | 0.5 | 32.0 | 23'40" | 25'40" | 2'00" |
|  | 1.0 | 31.0 | 28'40" | 32'50" | 4'10" |

As is proven by Table 2, the compounds in this invention are all very efficient in preventing prevulcanization.

TABLE 3

(a) at 140° C.

| Scorch Retardant | PHR | $t_{10}$ | $t_{90}$ | R | T |
|---|---|---|---|---|---|
| None | — | 5'30" | 14'10" | 8'40" | 22'50" |
| N—n-butylthio-N—cyclohexyl benzothiazole-2-sulfonamide | 0.5 | 8'55" | 17'00" | 8'05" | 25'05" |
|  | 1.0 | 11'15" | 17'35" | 6'20" | 23'55" |
| N—n-hexylthio-N—cyclohexyl benzothiazole-2-sulfonamide | 0.5 | 8'50" | 15'25" | 6'35" | 22'00" |
|  | 1.0 | 11'25" | 18'00" | 6'35" | 24'35" |
| N—n-octylthio-N—cyclohexyl benzothiazole-2-sulfonamide | 0.5 | 9'40" | 16'50" | 7'10" | 24'10" |
|  | 1.0 | 12'35" | 19'35" | 7'00" | 26'35" |
| N—n-dodecylthio-N—cyclohexyl benzothiazole-2-sulfonamide | 0.5 | 9'30" | 16'30" | 7'00" | 23'30" |
|  | 1.0 | 12'10" | 19'00" | 6'50" | 25'50" |
| N—phenylthio-N—cyclohexyl benzothiazole-2-sulfonamide | 0.5 | 8'50" | 16'40" | 7'50" | 24'30" |
|  | 1.0 | 11'25" | 18'50" | 7'25" | 26'15" |
| N—p-tolylthio-N—cyclohexyl benzothiazole-2-sulfonamide | 0.5 | 8'50" | 15'35" | 6'45" | 22'20" |
|  | 1.0 | 12'05" | 19'00" | 6'55" | 25'55" |
| N—cyclohexylthio-N—cyclohexyl benzothiazole-2-sulfonamide | 0.5 | 10'35" | 18'25" | 7'50" | 26'15" |
|  | 1.0 | 15'10" | 22'45" | 7'35" | 30'20" |
| N—cyclohexylthio-N—ethyl benzothiazole-2-sulfonamide | 1.0 | 14'55" | 26'55" | 12'00" | 28'55" |
| N—cyclohexylthio-N—phenyl benzothiazole-2-sulfonamide | 0.5 | 7'00" | 12'40" | 5'40" | 18'20" |
|  | 1.0 | 16'20" | 28'35" | 12'15" | 40'50" |
| N—cyclohexylthio-N—cyclohexyl-5-chlorobenzothiazole-2-sulfonamide | | | | | |
| Phthalic anhydride (for comparison) | 0.5 | 7'30" | 17'35" | 10'05" | 27'40" |
|  | 1.0 | 9'10" | 23'35" | 14'25" | 38'00" |
| N—nitrosodiphenylamine (for comparison) | 0.5 | 7'30" | 13'00" | 5'30" | 18'30" |
|  | 1.0 | 9'35" | 19'35" | 10'00" | 29'35" |

TABLE 3

(b) at 150° C.

| Scorch Retardant | PHR | $t_{10}$ | $t_{90}$ | R | T |
|---|---|---|---|---|---|
| None | — | 2'40" | 6'40" | 4'00" | 10'40" |
| N—n-butylthio-N—cyclohexyl benzothiazole-2-sulfonamide | 0.5 | 4'35" | 8'00" | 3'25" | 11'25" |
|  | 1.0 | 5'35" | 8'00" | 2'25" | 10'25" |
| N—n-hexylthio-N—cyclohexyl benzothiazole-2-sulfonamide | 0.5 | 4'25" | 7'10" | 2'45" | 9'55" |
|  | 1.0 | 5'50" | 8'05" | 2'15" | 10'20" |
| N—n-octylthio-N—cyclohexyl benzothiazole-2-sulfonamide | 0.5 | 4'50" | 7'35" | 2'45" | 10'20" |
|  | 1.0 | 6'10" | 8'50" | 2'40" | 11'30" |

TABLE 3-continued

(b) at 150° C.

| Scorch Retardant | PHR | $t_{10}$ | $t_{90}$ | R | T |
|---|---|---|---|---|---|
| N—n-dodecylthio-N—cyclohexyl benzothiazole-2-sulfonamide | 0.5 | 4'40" | 7'25" | 2'45" | 10'10" |
|  | 1.0 | 6'00" | 8'50" | 2'50" | 11'40" |
| N—phenylthio-N—cyclohexyl benzothiazole-2-sulfonamide | 0.5 | 4'20" | 6'40" | 2'20" | 9'00" |
|  | 1.0 | 5'20" | 8'00" | 2'40" | 10'40" |
| N—p-tolylthio-N—cyclohexyl benzothiazole-2-sulfonamide | 0.5 | 4'20" | 7'10" | 2'50" | 10'10" |
|  | 1.0 | 5'40" | 8'40" | 3'00" | 11'40" |
| N—cyclohexylthio-N—cyclohexyl benzothiazole-2-sulfonamide | 0.5 | 5'00" | 8'00" | 3'00" | 11'00" |
|  | 1.0 | 7'05" | 10'20" | 3'15" | 13'35" |
| N—cyclohexylthio-N—ethyl benzothiazole-2-sulfonamide | 1.0 | 8'00" | 11'50" | 3'50" | 15'40" |
| N—cyclohexylthio-N—phenyl benzothiazole-2-sulfonamide | 0.5 | 3'50" | 6'50" | 3'00" | 9'50" |
|  | 1.0 | 8'20" | 12'00" | 3'40" | 15'40" |
| N—cyclohexylthio-N—cyclohexyl-5-chlorobenzothiazole-2-sulfonamide | 0.5 | 3'50" | 7'10" | 3'20" | 10'30" |
| Phthalic anhydride (for comparison) | 1.0 | 4'25" | 11'50" | 7'25" | 19'15" |
| N—nitrosodiphenylamine (for comparison) | 0.5 | 3'50" | 5'35" | 1'45" | 7'20" |
|  | 1.0 | 4'35" | 8'40" | 4'05" | 12'45" |

TABLE 4

(140° C. × 25 min., press cure)

| Scorch Retardant | PHR | Tensile strength (kg/cm$^2$) | Elongation (%) | 300% Modulus (kg/cm$^2$) | Hardness (JIS)* |
|---|---|---|---|---|---|
| None | — | 264 | 486 | 163 | 72 |
| N—cyclohexylthio-N—cyclohexyl benzothiazole-2-sulfonamide | 0.25 | 252 | 467 | 152 | 72 |
|  | 0.5 | 263 | 497 | 161 | 72 |
|  | 0.75 | 273 | 545 | 172 | 72 |
| N—n-octylthio-N—cyclohexyl benzothiazole-2-sulfonamide | 0.25 | 279 | 497 | 180 | 72.5 |
|  | 0.5 | 275 | 467 | 186 | 72.5 |
|  | 0.75 | 275 | 513 | 181 | 72 |
| N—n-dodecylthio-N—cyclohexyl benzothiazole-2-sulfonamide | 0.25 | 261 | 454 | 177 | 72 |
|  | 0.5 | 262 | 473 | 173 | 72 |
|  | 0.75 | 264 | 477 | 168 | 72 |
| N—n-butylthio-N—cyclohexyl benzothiazole-2-sulfonamide | 0.25 | 257 | 476 | 149 | 72 |
|  | 0.5 | 261 | 488 | 162 | 72 |
|  | 0.75 | 268 | 507 | 166 | 72 |
| Phthalic anhydride (for comparison) | 0.5 | 255 | 504 | 145 | 70 |
|  | 1.0 | 245 | 552 | 138 | 69.5 |
| N—nitrosodiphenylamine (for comparison) | 0.5 | 272 | 561 | 153 | 70 |
|  | 1.0 | 256 | 531 | 135 | 69 |

*Japanese Industrial Standard

EXAMPLE 9

The scorch retardants of the invention are tested by the methods described above with the recipe shown in Table 5. The results of Mooney scorch and curelastometer test at 140° C. are shown in Tables 6 and 7 respectively.

TABLE 5

| | |
|---|---|
| Natural rubber | 100 parts by wt |
| Zinc Oxide | 5 |
| Sulfur | 2.5 |
| Stearic acid | 1 |
| Process oil | 5 |
| Carbon black (HAF) | 50 |
| Accelerator | variable |
| Scorch retardant | variable |

TABLE 6

(ML$_1$, 120° C.)

| Accelerator (PHR) | | Scorch Retardant | (PHR) | $V_m$ | $t_5$ | $t_{35}$ | $t_{\Delta 30}$ |
|---|---|---|---|---|---|---|---|
| MBTS[1] + 0.7 | DPG[2] 0.3 | None | — | 32.0 | 9'10" | 10'50" | 1'40" |
|  |  | OCBS[3] | 0.5 | 32.0 | 12'20" | 14'55" | 2'35" |
|  |  |  | 1.0 | 33.0 | 18'00" | 21'05" | 3'05" |
|  |  | DCBS[4] | 0.5 | 31.0 | 11'55" | 14'10" | 2'15" |
|  |  |  | 1.0 | 31.0 | 17'05" | 19'05" | 2'00" |
|  |  | CCBS[5] | 0.5 | 29.0 | 11'35" | 14'15" | 2'40" |
|  |  |  | 1.0 | 30.0 | 19'00" | 23'00" | 4'05" |
|  |  | Phthalic anydride (for comparison) | 0.5 | 31.0 | 12'55" | 15'10" | 2'15" |
|  |  |  | 1.0 | 28.5 | 15'50" | 19'45" | 3'55" |
|  |  | N—nitrosodiphenylamine (for comparison) | 0.5 | 30.0 | 12'00" | 14'30" | 2'30" |
|  |  |  | 1.0 | 31.0 | 13'20" | 16'40" | 3'20" |
| MBTS[1] | 0.7 | None | — | 37.0 | 15'50" | 19'00" | 3'10" |
|  |  | CCBS[5] | 1.0 | 34.0 | 31'55" | 43'35" | 12'00" |
| TMTD[6] | 0.3 | None | — | 36.5 | 9'05" | 10'00" | 55" |
|  |  | OCBS[3] | 0.5 | 32.0 | 15'50" | 17'10" | 1'20" |
|  |  |  | 1.0 | 33.0 | 22'15" | 23'20" | 1'05" |
|  |  | DCBS[4] | 0.5 | 36.0 | 16'05" | 17'20" | 1'15" |
|  |  |  | 1.0 | 33.0 | 24'55" | 25'50" | 55" |
|  |  | CCBS[5] | 0.5 | 35.0 | 15'00" | 16'55" | 1'55" |

TABLE 6-continued

| Accelerator (PHR) | Scorch Retardant | (PHR) | $V_m$ | $t_5$ | $t_{35}$ | $t_{\Delta 30}$ |
|---|---|---|---|---|---|---|
| | | 1.0 | 35.0 | 22'25" | 24'05" | 1'40" |
| | Phthalic anhydride | 0.5 | 35.0 | 11'35" | 12'55" | 1'20" |
| | (for comparison) | 1.0 | 34.5 | 11'00" | 12'55" | 1'25" |
| | N—nitrosodiphenylamine | 0.5 | 32.0 | 10'00" | 12'15" | 2'15" |
| | (for comparison) | 1.0 | 35.0 | 11'35" | 14'15" | 2'40" |

(ML$_1$, 120° C.)

Notes:
[1] Dibenzothiazyl disulfide
[2] 1,3-diphenylguanidine
[3] N—n-octylthio-N—cyclohexyl benzothiazole-2-sulfonamide (inventive compound)
[4] N—n-dodecylthio-N-cyclohexyl benzothiazole-2-sulfonamide (inventive compound)
[5] N—cyclohexylthio-N—cyclohexyl benzothiazole-2-sulfonamide (inventive compound)
[6] Tetramethylthiuram disulfide

TABLE 7 at 140° C.

| Accelerator (PHR) | | Scorch Retardant | (PHR) | $t_{10}$ | $t_{90}$ | R | T |
|---|---|---|---|---|---|---|---|
| MBTS[1] + | DPG[2] | None | — | 2'40" | 6'00" | 3'20" | 9'20" |
| 0.7 | 0.3 | OCBS[3] | 0.5 | 3'40" | 10'30" | 6'50" | 17'20" |
| | | | 1.0 | 5'10" | 14'00" | 8'50" | 22'50" |
| | | DCBS[4] | 0.5 | 3'35" | 10'00" | 6'25" | 16'25" |
| | | | 1.0 | 4'45" | 13'15" | 8'30" | 21'45" |
| | | CCBS[5] | 0.5 | 3'30" | 12'00" | 8'30" | 20'30" |
| | | | 1.0 | 5'40" | 14'50" | 9'10" | 24'00" |
| | | Phthalic anhydride | 0.5 | 3'35" | 8'35" | 5'00" | 13'35" |
| | | (for comparison) | 1.0 | 4'45" | 18'00" | 13'15" | 31'15" |
| | | N—nitrosodiphenylamine | 0.5 | 3'50" | 7'40" | 3'50" | 11'30" |
| | | (for comparison) | 1.0 | 4'40" | 14'00" | 9'20" | 23'20" |
| MBTS[1] | 0.7 | None | — | 4'05" | 18'35" | 14'30" | 33'05" |
| | | CCBS[5] | 1.0 | 8'00" | 24'40" | 16'40" | 41'20" |
| TMTD[6] | 0.3 | None | — | 2'15" | 6'25" | 4'10" | 10'35" |
| | | OCBS[3] | 0.5 | 4'20" | 8'00" | 3'40" | 11'40" |
| | | | 1.0 | 6'25" | 9'45" | 3'20" | 13'05" |
| | | DCBS[4] | 0.5 | 4'35" | 7'40" | 3'05" | 10'45" |
| | | | 1.0 | 7'10" | 10'40" | 3'30" | 14'10" |
| | | CCBS[5] | 0.5 | 4'15" | 7'40" | 3'25" | 11'05" |
| | | | 1.0 | 6'20" | 9'20" | 2'55" | 12'15" |
| | | Phthalic anhydride | 0.5 | 3'20" | 5'00" | 1'40" | 6'40" |
| | | (for comparison) | 1.0 | 3'10" | 5'35" | 2'25" | 8'00" |
| | | N—nitrosodiphenylamine | 0.5 | 3'20" | 7'00" | 3'40" | 10'40" |
| | | (for comparison) | 1.0 | 4'00" | 8'50" | 4'50" | 13'40" |

Notes:
[1] Dibenzothiazyl disulfide
[2] 1,3-diphenylguanidine
[3] N—n-octylthio-N—cyclohexyl benzothiazole-2-sulfonamide (inventive compound)
[4] N—n-dodecylthio-N-cyclohexyl benzothiazole-2-sulfonamide (inventive compound)
[5] N—cyclohexylthio-N—cyclohexyl benzothiazole-2-sulfonamide (inventive compound)
[6] Tetramethylthiuram disulfide

EXAMPLE 10

Using the recipe shown in Table 8, the scorch inhibition and the curing characteristics of the scorch retardants of the invention are tested according to the techniques of Example 8.

Recipe is shown in Table 8. Tables 9 and 10 illustrate the results of using N-substituted benzothiazole-2-sulfonamides as scorch retardants in stocks of SBR.

TABLE 8

| JSR CH50[1] | 162 parts by wt |
|---|---|
| Zinc oxide | 3 |
| Sulfur | 2 |
| Accelerator CBS[2] | 1 |
| Accelerator DPG | 0.3 |
| Antioxidant[3] | 1 |
| Anti-scorch agent | variable |

Notes:
[1] SBR 1502: 100; carbon black (HAF): 50; stearic acid: 3; Naphthenic process oil: 9; all by wt.
[2] N—cyclohexylbenzothiazole-2-sulfenamide
[3] N—isopropyl-N'—phenyl-P—phenylenediamine

TABLE 9

(ML$_1$ 120° C.)

| Scorch Retardant | PHR | $M_v$ | $t_5$ | $t_{35}$ | $t_{\Delta 30}$ |
|---|---|---|---|---|---|
| None | — | 32.0 | 31'05" | 40'15" | 9'10" |
| N—n-butylthio-N—cyclohexyl benzothiazole-2-sulfonamide | 0.5 | 32.0 | 47'35" | 56'05" | 8'30" |
| | 1.0 | 32.0 | 48'25" | 55'45" | 7'20" |
| N—n-hexylthio-N—cyclohexyl benzothiazole-2-sulfonamide | 0.5 | 32.0 | 46'10" | 54'10" | 7'30" |
| | 1.0 | 32.0 | 46'40" | 53'05" | 6'25" |
| N—n-octylthio-N—cyclohexyl benzothiazole-2-sulfonamide | 0.5 | 31.0 | 43'35" | 52'10" | 8'35" |
| | 1.0 | 30.0 | 46'25" | 52'05" | 5'40" |
| N—n-dodecylthio-N—cyclohexyl benzothiazole-2-sulfonamide | 0.5 | 32.5 | 44'00" | 52'05" | 8'05" |
| | 1.0 | 36.0 | 47'50" | 55'35" | 7'45" |
| N—phenylthio-N—cyclohexyl benzothiazole-2-sulfonamide | 0.5 | 35.0 | 44'25" | 51'40" | 7'15" |
| | 1.0 | 35.0 | 56'40" | 63'25" | 6'45" |
| N—p-tolylthio-N—cyclohexyl | 0.5 | 33.0 | 46'25" | 54'10" | 7'45" |

TABLE 9-continued

| Scorch Retardant | PHR | $M_v$ | $t_5$ | $t_{35}$ | $t_{\Delta 30}$ |
|---|---|---|---|---|---|
| benzothiazole-2-sulfonamide | 1.0 | 33.0 | 52'00" | 61'00" | 9'00" |
| N—cyclohexylthio-N—cyclohexyl benzothiazole-2-sulfonamide | 0.5 | 33.0 | 51'10" | 61'35" | 10'25" |
|  | 1.0 | 33.0 | 66'20" | 77'30" | 11'10" |
| Phthalic anhydride (for comparison) | 0.5 | 36.0 | 34'00" | 43'40" | 9'40" |
|  | 1.0 | 31.0 | 39'00" | 50'35" | 11'35" |
| N—nitrosodiphenylamine (for comparison) | 0.5 | 29.0 | 30'10" | 58'10" | 28'00" |
|  | 1.0 | 31.0 | 36'30" | 49'00" | 12'30" |

(ML₁ 120° C.) header applies above.

As seen from Table 9, the compounds of the invention are all very efficient in preventing prevulcanization.

TABLE 10 at 150° C.

| Scorch Retardant | PHR | $t_{10}$ | $t_{90}$ | R | T |
|---|---|---|---|---|---|
| None | — | 6'00" | 16'10" | 10'10" | 26'20" |
| N—n-butylthio-N—cyclohexyl benzothiazole-2-sulfonamide | 0.5 | 8'00" | 17'35" | 9'35" | 27'10" |
|  | 1.0 | 8'50" | 18'10" | 9'20" | 27'30" |
| N—n-hexylthio-N—cyclohexyl benzothiazole-2-sulfonamide | 0.5 | 8'05" | 18'25" | 10'20" | 28'45" |
|  | 1.0 | 8'10" | 18'10" | 10'00" | 28'10" |
| N—n-octylthio-N—cyclohexyl benzothiazole-2-sulfonamide | 0.5 | 7'55" | 18'30" | 10'35" | 29'05" |
|  | 1.0 | 8'25" | 18'30" | 10'05" | 28'35" |
| N—n-dodecylthio-N—cyclohexyl benzothiazole-2-sulfonamide | 0.5 | 8'10" | 18'35" | 10'25" | 29'00" |
|  | 1.0 | 8'55" | 19'20" | 10'25" | 29'45" |
| N—phenylthio-N—cyclohexyl benzothiazole-2-sulfonamide | 0.5 | 7'55" | 17'55" | 10'00" | 27'55" |
|  | 1.0 | 9'45" | 20'10" | 10'25" | 30'35" |
| N—p-Tolylthio-N—cyclohexyl benzothiazole-2-sulfonamide | 0.5 | 8'25" | 18'50" | 10'25" | 29'15" |
|  | 1.0 | 9'45" | 20'10" | 10'25" | 30'35" |
| N—cyclohexylthio-N—cyclohexyl benzothiazole-2-sulfonamide | 0.5 | 9'50" | 20'10" | 10'20" | 30'30" |
|  | 1.0 | 12'15" | 22'40" | 10'25" | 33'05" |
| Phthalic anhydride (for comparison) | 0.5 | 6'55" | 19'10" | 12'15" | 31'25" |
|  | 1.0 | 7'50" | 22'35" | 14'45" | 37'20" |
| N—nitrosodiphenylamine (for comparison) | 0.5 | 6'15" | 18'00" | 11'45" | 29'45" |
|  | 1.0 | 7'35" | 20'25" | 12'50" | 33'15" |

EXAMPLE 11

Compounded rubber consisting of: smoked sheet 100; zinc oxide 5; sulfur 2.5; stearic acid 1; process oil 5; and accelerator CBS (N-cyclohexylbenzothiazole-2-sulfenamide) 0.7, all parts by weight, is heat treated for 10 days in a Geer Oven at 50°±5° C.

A Mooney scorch test and curelastometer test are carried out as in Example 1 at 140° C. The results before and after heat treatment are shown in Table 11.

0.5 PHR antiscorch agents of the invention and conventional antiscorch agents are added respectively to the compounded rubber mixture and remasticated.

The results of the Mooney scorch test at 120° C. and curelastometer test at 140° C. are shown in Table 12 for a number of retardants.

TABLE 11

| Heat treatment | Before | After |
|---|---|---|
| Mooney Scorch ML, 120° C. | | |
| Minimum viscosity | 49 | 54.0 |
| $t_5$ (min, sec) | 20'40" | 12'50" |
| $t_{35}$ (min, sec) | 22'20" | 15'20" |
| $t_{\Delta 30}$ (min, sec) | 1'40" | 2'30" |
| Curelastometer Test 140° C. | | |
| $t_{10}$ (min, sec) | 6'10" | 4'00" |
| $t_{90}$ (min, sec) | 15'30" | 15'50" |
| R (min, sec) | 9'20" | 11'50" |
| T (min, sec) | 24'50" | 27'40" |

TABLE 12

| Item | OCBS¹ (inventive) | DCBS² (inventive) | CCBS³ (inventive) | Phthalic anhydride (comparison) | N—nitrosodiphenylamine (comparison) |
|---|---|---|---|---|---|
| Mooney Scorch Test - ML₁, 120° C. | | | | | |
| Minimum Viscosity | 31.0 | 30.0 | 30.0 | 33.0 | 35.0 |
| $t_5$ (min, sec) | 25'10" | 24'30" | 24'25" | 15'25" | 15'10" |
| $t_{35}$ (min, sec) | 28'10" | 28'05" | 28'40" | 22'25" | 22'00" |
| $t_{\Delta 30}$ (min, sec) | 3'30" | 3'35" | 4'15" | 7'00" | 6'50" |
| Curelastometer Test - 140° C. | | | | | |
| $t_{10}$ (min, sec) | 7'25" | 7'05" | 7'35" | 5'20" | 5'25" |
| $t_{90}$ (min, sec) | 16'10" | 16'00" | 16'50" | 20'00" | 13'35" |
| R (min, sec) | 8'45" | 8'55" | 8'15" | 14'40" | 12'10" |
| T (min, sec) | 24'55" | 24'55" | 25'05" | 29'40" | 25'45" |

Notes:
¹N—n-octylthio-N—cyclohexyl benzothiazole-2-sulfonamide
²N—n-dodecylthio-N—cyclohexyl benzothiazole-2-sulfonamide
³N—n-cyclohexylthio-N—cyclohexyl benzothiazole-2-sulfonamide From the results of Tables 11 and 12, it is obvious that the scorch retardants of the invention are all very superior to the conventional scorch retardants in reducing the viscosity of scorched rubber. The scorch retarders of the invention are thus useful in reclaiming the scorched rubber.

EXAMPLE 12

According to the method shown in Example 8, the scorch inhibition and curing characteristics of the scorch retardants of the invention are tested. The recipe is shown in Table 13.

Tables 14 and 15 illustrate the use of N-substituted benzothiazole-2-sulfonamides as scorch retardants in stocks of chloroprene rubber containing metal oxide and accelerator (Trithiocyanuric Acid). The crosslinking curve is shown in FIG. 1.

TABLE 13

| Chloroprene rubber* | 100 parts by wt |
|---|---|
| Zinc oxide | 5 |

TABLE 13-continued

| | |
|---|---|
| Magnesium oxide | 4 |
| Stearic acid | 1 |
| Naphtenic process oil | 10 |
| Carbon black (SFR) | 50 |
| Accelerator (Trithiocyanuric acid) | 1.5 |
| Scorch retardant | variable |

*Neoprene W (product of Showa neoprene Co.)

TABLE 14

| | | (ML$_1$, 120° C.) | | |
|---|---|---|---|---|
| Scorch Retardant | PHR | M$_v$ | t$_5$ | t$_{35}$ | t$_{\Delta 30}$ |
| None | — | 52.0 | 3'05" | 11'30" | 8'25" |
| N—n-butylthio-N—cyclohexyl benzothiazole-2-sulfonamide | 0.5 | 40.5 | 10'50" | 21'25" | 10'35" |
| | 1.0 | 39.0 | 10'05" | 29'20" | 19'15" |
| N—n-hexylthio-N—cyclohexyl benzothiazole-2-sulfonamide | 0.5 | 39.5 | 7'55" | 24'25" | 16'30" |
| | 1.0 | 39.0 | 9'35" | 26'35" | 17'00" |
| N—n-octylthio-N—cyclohexyl benzothiazole-2-sulfonamide | 0.5 | 37.0 | 11'20" | 29'05" | 17'45" |
| | 1.0 | 36.0 | 12'05" | 26'30" | 14'25" |
| N-n-dodecylthio-N—cyclohexyl benzothiazole-2-sulfonamide | 0.5 | 39.0 | 11'20" | 27'25" | 16'05" |
| | 1.0 | 37.0 | 12'50" | 32'00" | 19'10" |
| N—phenylthio-N—cyclohexyl benzothiazole-2-sulfonamide | 0.5 | 40.0 | 7'35" | 23'00" | 15'25" |
| | 1.0 | 43.0 | 10'30" | 25'10" | 14'40" |
| N—p-tolylthio-N—cyclohexyl benzothiazole-2-sulfonamide | 0.5 | 43.5 | 7'55" | 22'30" | 14'35" |
| | 1.0 | 39.0 | 10'00" | 26'50" | 16'50" |
| N—cyclohexylthio-N—cyclohexyl benzothiazole-2-sulfonamide | 0.5 | 41.0 | 6'50" | 23'10" | 16'20" |
| | 1.0 | 39.0 | 9'10" | 29'00" | 19'50" |
| N—cyclohexylthio-N—cyclohexyl-5-chlorobenzothiazole-2-sulfonamide | 1.0 | 41.0 | 7'30" | 25'00" | 17'20" |
| N—cyclohexylthio-N—ethyl benzothiazole-2-sulfonamide | 1.0 | 36.0 | 8'00" | 27'10" | 19'10" |
| N—cyclohexylthio-N—phenyl benzothiazole-2-sulfonamide | 1.0 | 37.0 | 6'20" | 27'10" | 20'50" |
| Dibenzothiazyl disulfide (for comparison) | 0.5 | 42.0 | 5'55" | 14'30" | 8'35" |
| | 1.0 | 39.0 | 5'55" | 15'20" | 9'25" |

It is thus seen that the inventive compounds are very effective and efficient in preventing prevulcanization.

TABLE 15

| | | (160° C.) | | | |
|---|---|---|---|---|---|
| Scorch Retardant | PHR | t$_{10}$ | t$_{90}$ | R | T |
| None | — | 1'10" | 32'00" | 30'50" | 62'50" |
| N—n-butylthio-N—cyclohexyl benzothiazole-2-sulfonamide | 0.5 | 2'45" | 26'35" | 23'50" | 50'25" |
| | 1.0 | 3'10" | 25'35" | 22'25" | 48'00" |
| N—n-hexylthio-N—cyclohexyl benzothiazole-2-sulfonamide | 0.5 | 2'45" | 26'40" | 23'55" | 50'35" |
| | 1.0 | 3'00" | 25'00" | 22'00" | 47'00" |
| N—n-octylthio-N—cyclohexyl benzothiazole-2-sulfonamide | 0.5 | 2'45" | 28'50" | 26'05" | 54'55" |
| | 1.0 | 2'55" | 27'30" | 24'35" | 52'05" |
| N—n-dodecylthio-N—cyclohexyl benzothiazole-2-sulfonamide | 0.5 | 2'40" | 29'00" | 26'20" | 55'20" |
| | 1.0 | 3'00" | 30'35" | 27'35" | 58'10" |
| N—phenylthio-N—cyclohexyl benzothiazole-2-sulfonamide | 0.5 | 2'30" | 26'00" | 23'30" | 49'30" |
| | 1.0 | 3'00" | 24'50" | 21'50" | 46'40" |
| N—p-tolylthio-N—cyclohexyl benzothiazole-2-sulfonamide | 0.5 | 2'35" | 28'00" | 25'25" | 53'25" |
| | 1.0 | 2'55" | 27'35" | 24'40" | 52'15" |
| N—cyclohexylthio-N—cyclohexyl benzothiazole-2-sulfonamide | 0.5 | 2'35" | 30'20" | 27'45" | 58'05" |
| | 1.0 | 2'50" | 30'50" | 28'00" | 58'50" |
| N—cyclohexylthio-N—cyclohexyl-5-chlorobenzothiazole-2-sulfonamide | 1.0 | 2'25" | 33'50" | 31'25" | 65'15" |
| N—cyclohexylthio-N—ethyl benzothiazole-2-sulfonamide | 1.0 | 2'20" | 36'00" | 33'40" | 69'40" |
| N—cyclohexylthio-N—phenyl benzothiazole-2-sulfonamide | 1.0 | 2'35" | 28'10" | 25'35" | 53'45" |
| Dibenzothiazyl disulfide (for comparison) | 0.5 | 1'35" | 29'10" | 27'35" | 56'45" |
| | 1.0 | 1'20" | 30'20" | 29'00" | 59'20" |

EXAMPLE 13

The effects of the inventive compounds on accelerators was tested according to the method shown in Example 12.

The recipe used is shown in Table 16. The result of Mooney scorch test at 120° C. and curelastometer test at 160° C. are shown in Tables 17 and 18 respectively.

TABLE 16

| RECIPE | |
|---|---|
| Chloroprene rubber* | 100 parts by wt |
| Zinc oxide | 5 |
| Magnesium oxide | 4 |
| Stearic acid | 1 |
| Carbon black (SRF) | 50 |
| Process oil | 10 |
| Accelerator | variable |
| Scorch retardant | variable |

*Neoprene W (Product of Showa Neoprene Co.)

TABLE 17

| | | | (ML$_1$, 120° C.) | | |
|---|---|---|---|---|---|
| Accelerator | Scorch Retardant | PHR | M$_v$ | t$_5$ | t$_{35}$ | t$_{\Delta 30}$ |
| 2-dibutylamino-4,6-dimercapto-S—triazine (1.5 PHR) | None | — | 52.5 | 3'20" | 7'25" | 4'05" |
| | DCBS[1] | 0.5 | 47.5 | 4'10" | 11'25" | 7'15" |
| | DCBS[1] | 1.0 | 46.0 | 8'35" | 26'00" | 17'25" |
| | MBTS[2] (for comparison) | 0.5 | 51.0 | 3'50" | 9'30" | 5'40" |
| | | 1.0 | 42.5 | 2'35" | 4'50" | 2'15" |
| Diethylthiourea (1.0 PHR) | None | — | 38.0 | 7'30" | 13'10" | 5'40" |
| | DCBS[1] | 1.0 | 34.0 | 12'25" | 16'40" | 4'15" |
| DMTT[3] (1.0 PHR) | None | — | 34.0 | 15'30" | 45'20" | 29'50" |
| | DCBS[1] | 1.0 | 33.5 | 16'20" | 50'45" | 34'25" |
| DAPM[4] (1.0 PHR) | None | — | 37.5 | 13'00" | 30'50" | 17'50" |
| | DCBS[1] | 1.0 | 39.0 | 14'25" | 32'30" | 18'05" |
| Diak No. 1[5] (1.0 PHR) | None | — | 49.0 | 6'40" | 16'05" | 9'25" |
| | DCBS[1] | 1.0 | 45.0 | 8'40" | 22'35" | 13'55" |
| DMTZ[6] (1.0 PHR) | None | — | 52.0 | 3'00" | 6'30" | 3'30" |
| | DCBS[1] | 1.0 | 45.0 | 3'55" | 7'05" | 3'10" |

Notes:
[1]N—n-dodecylthio-N—cyclohexyl benzothiazole-2-sulfonamide (inventive compound)
[2]Dibenzothiazyl disulfide
[3]Tetrahydro-3,5-dimethyl-2H—1,3,5-thiazine-2-thione
[4]P,P'—diaminodiphenylmethane
[5]Hexamethylenediamine carbamate (Du Pont Co.)
[6]2,5-dimercapto-1,3,4 thiaziazole

TABLE 18

(160° C.)

| Accelerator | Scorch Retardant | PHR | $t_{10}$ | $t_{90}$ | R | T |
|---|---|---|---|---|---|---|
| 2-dibutyl-amino-4,6-dimercapto-S—triazine (1.5 PHR) | None | — | 50″ | 9′50″ | 9′10″ | 18′50″ |
| | DCBS[1] | 0.5 | 55″ | 3′30″ | 2′35″ | 6′05″ |
| | DCBS[1] | 1.0 | 1′05″ | 7′40″ | 6′35″ | 14′15″ |
| | MBTS[2] | 0.5 | 10″ | 5′50″ | 5′40″ | 11′30″ |
| (for comparison) | | 1.0 | 20″ | 16′00″ | 15′40″ | 31′40″ |
| Diethyl-thiourea (1.0 PHR) | None | — | 1′20″ | 23′00″ | 21′40″ | 44′40″ |
| | DCBS[1] | 1.0 | 1′30″ | 15′10″ | 13′40″ | 28′50″ |
| DMTT[3] (1.0 PHR) | None | — | 4′30″ | 28′10″ | 29′40″ | 51′50″ |
| | DCBS[1] | 1.0 | 4′40″ | 23′30″ | 18′50″ | 42′20″ |
| DAPM[4] (1.0 PHR) | None | — | 3′40″ | 37′00″ | 33′20″ | 70′20″ |
| | DCBS[1] | 1.0 | 4′00″ | 38′25″ | 34′25″ | 72′50″ |
| Diak No. 1[5] (1.0 PHR) | None | — | 2′00″ | 28′20″ | 26′20″ | 54′40″ |
| | DCBS[1] | 1.0 | 2′55″ | 34′00″ | 31′05″ | 65′05″ |
| DMTZ[6] (1.0 PHR) | None | — | 50″ | 21′15″ | 20′25″ | 41′40″ |
| | DCBS[1] | 1.0 | 1′00″ | 30′30″ | 29′30″ | 60′00″ |

Notes:
[1]N—n-dodecylthio-N—cyclohexyl benzothiazole-2-sulfonamide (inventive compound)
[2]Dibenzothiazyl disulfide
[3]Tetrahydro-3,5-dimethyl-2H—1,3,5-thiazine-2-thione
[4]p,p'—diaminodiphenylmethane
[5]Hexamethylenediamine carbamate (Du Pont Co.)
[6]2,5-dimercapto-1,3,4 thiaziazole

EXAMPLE 14

As in Example 13, the anti-scorch effect and the influence on the cure rate of the compounds of the invention for Epichlorohydrin rubber (CHR 100), Epichlorohydrin ethylene oxide copolymer rubber (CHC 200) and Chlorinated polyethylene (CPE) are tested in Tables 19, 22, and 24.

Comparative tests of vulcanization according to JISK 6301 (1975) are shown in Tables 20 and 23.

Results of heat aging tests in a Geer oven at 150° C. for 72 hours are shown in Table 21.

TABLE 19

| Compounds | 1 | 2 | 3 | 4 | 5 |
|---|---|---|---|---|---|
| CHR 100[1] | 100 | 100 | 100 | 100 | 100 |
| Magnesium oxide | 5 | 5 | 5 | 5 | 5 |
| Tin stearate | 1 | 1 | 1 | 1 | 1 |
| Carbon black (FEF) | 40 | 40 | 40 | 40 | 40 |
| DPG[2] | 0.5 | 0.5 | 0.5 | 0.5 | 0.5 |
| TTCA[3] | 2 | 2 | 2 | 2 | 2 |
| OCBS[4] | — | 1.0 | — | — | — |
| DCBS[5] | — | — | 1.0 | — | — |
| CCBS[6] | — | — | — | 1.0 | — |
| MBTS[7] (for comparison) | — | — | — | — | 1.0 |
| Mooney Scorch Test - ML₁, 125° C. | | | | | |
| Minimum Viscosity | 37.0 | 37.0 | 35.0 | 24.0 | 37.0 |
| $t_5$ (min, sec) | 12′50″ | 28′10″ | 31′10″ | 41′25″ | 16′50″ |
| $t_{35}$ (min, sec) | 27′25″ | 41′50″ | 47′50″ | 67′10″ | 38′10″ |
| $t_{\Delta 30}$ (min, sec) | 14′35″ | 13′40″ | 16′40″ | 25′45″ | 21′20″ |
| Curastometer Test - 160° | | | | | |
| $t_{10}$ (min, sec) | 2′25″ | 3′30″ | 3′20″ | 4′00″ | 3′20″ |
| $t_{90}$ (min, sec) | 38′30″ | 38′35″ | 36′00″ | 36′35″ | 33′50″ |
| R (min, sec) | 36′05″ | 35′05″ | 32′40″ | 32′35″ | 30′30″ |
| T (min, sec) | 74′35″ | 73′40″ | 68′40″ | 69′10″ | 64′20″ |

Notes:
[1]Epichlorohydrine rubber (Product of Goodrich Co.)
[2]1,3-diphenylguanidine
[3]Trithiocyanuric acid
[4]N—n-octylthio-N—cyclohexyl benzothiazole-2-sulfonamide (inventive compound)
[5]N—n-dodecylthio-N—cyclohexyl benzothiazole-2-sulfonamide (inventive compound)
[6]N—n-cyclohexylthio-N—cyclohexyl benzothiazole-2-sulfonamide (inventive compound)
[7]Dibenzothiazyl disulfide As seen from the above, the inventive compounds are all very efficient in preventing prevulcanization.

TABLE 20

| | Conditions | 1 | 2 | 3 | 4 | 5 |
|---|---|---|---|---|---|---|
| Tensile Strength (kg/cm²) | 160° C. × 30 min | 150 | 147 | 146 | 151 | 131 |
| | 160° C. × 40 min | 151 | 149 | 150 | 154 | 139 |
| | 160° C. × 50 min | 148 | 148 | 153 | 156 | 1423 |
| Elongation (%) | 160° C. × 30 min | 222 | 232 | 270 | 245 | 467 |
| | 160° C. × 40 min | 174 | 191 | 205 | 180 | 368 |
| | 160° C. × 50 min | 143 | 152 | 163 | 161 | 308 |
| 100% Modulus (kg/cm²) | 160° C. × 30 min | 99 | 92 | 83 | 96 | 54 |
| | 160° C. × 40 min | 114 | 95 | 94 | 108 | 68 |
| | 160° C. × 50 min | 130 | 111 | 103 | 116 | 72 |
| Hardness (JIS)* | 160° C. × 30 min | 85 | 84 | 84 | 86 | 81 |
| | 160° C. × 40 min | 87 | 85.5 | 86 | 87.0 | 82 |
| | 160° C. × 50 min | 88 | 86 | 86 | 88 | 84 |

*JIS: Japanese Industrial Standard

TABLE 21

150° C. × 72 hours (160° C. × 40 min. press cure)

| Characteristics | | 1 | 2 | 3 | 4 | 5 |
|---|---|---|---|---|---|---|
| Tensile Strength (kg/cm²) | Before aging | 151 | 149 | 150 | 154 | 139 |
| | After aging | 139 | 132 | 136 | 129 | 135 |
| | Change (%) | −8 | −12 | −9 | −16 | −3 |
| Elongation (%) | Before aging | 174 | 191 | 205 | 180 | 368 |
| | After aging | 109 | 109 | 119 | 111 | 162 |
| | Change (%) | −38 | −43 | −42 | −38 | −56 |
| 100% Modulus (kg/cm²) | Before aging | 114 | 95 | 94 | 108 | 68 |
| | After aging | — | — | — | — | — |
| | Change (%) | — | — | — | — | — |
| Hardness (JIS)* | Before aging | 87 | 85.5 | 86 | 87 | 82.5 |
| | After aging | 88 | 88 | 88 | 88 | 87 |
| | Change (units) | +1 | +2.5 | +2 | +1 | +4.5 |

*JIS: Japanese Industrial Standard

TABLE 22

| Compounds | 6 | 7 | 8 | 9 | 10 |
|---|---|---|---|---|---|
| CHC 200[1] | 100 | 100 | 100 | 100 | 100 |
| Magnesium oxide | 5 | 5 | 5 | 5 | 5 |
| Tin stearate | 1 | 1 | 1 | 1 | 1 |
| Carbon black (FEF) | 40 | 40 | 40 | 40 | 40 |
| DPG[2] | 0.5 | 0.5 | 0.5 | 0.5 | 0.5 |
| TTCA[3] | 2 | 2 | 2 | 2 | 2 |
| OCBS[4] | — | 1.0 | — | — | — |
| DCBS[5] | — | — | 1.0 | — | — |
| CCBS[6] | — | — | — | 1.0 | — |
| MBTS[7] (for comparison) | — | — | — | — | 1.0 |
| Mooney Scorch Test - ML₁, 125° C. | | | | | |
| Minimum Viscosity | 78.0 | 53.0 | 66.0 | 62.0 | 74.0 |
| $t_5$ (min, sec) | 3′55″ | 7′00″ | 7′50″ | 9′20″ | 4′05″ |
| $t_{35}$ (min, sec) | 7′10″ | 13′55″ | 14′55″ | 17′20″ | 8′55″ |
| $t_{\Delta 30}$ (min, sec) | 3′15″ | 6′55″ | 7′05″ | 8′00″ | 4′50″ |
| Curelastometer Test - 160° | | | | | |
| $t_{10}$ (min, sec) | 1′20″ | 1′50″ | 1′55″ | 2′10″ | 1′40″ |
| $t_{90}$ (min, sec) | 21′35″ | 11′35″ | 12′00″ | 13′20″ | 23′35″ |
| R (min, sec) | 20′15″ | 9′45″ | 10′05″ | 11′10″ | 21′55″ |

TABLE 22-continued

| Compounds | 6 | 7 | 8 | 9 | 10 |
|---|---|---|---|---|---|
| T (min, sec) | 41'50" | 21'20" | 22'05" | 24'30" | 45'30" |

Notes:
[1] Epichlorohydrin ethylene oxide copolymer rubber
[2] 1,3-diphenylguanidine
[3] Trithiocyanuric acid
[4] N—n-octylthio-N—cyclohexyl benzothiazole-2-sulfonamide (inventive compound)
[5] N—n-dodecylthio-N—cyclohexyl benzothiazole-2-sulfonamide (inventive compound)
[6] N—n-cyclohexylthio-N—cyclohexyl benzothiazole-2-sulfonamide (inventive compound)
[7] Dibenzothiazyl disulfide The above results illustrate that the inventive compounds are very efficient in preventing prevulcanization.

TABLE 23

| | Conditions | 6 | 7 | 8 | 9 | 10 |
|---|---|---|---|---|---|---|
| Tensile | 160° C. × 20 min | 121 | 115 | 119 | 109 | 123 |
| Strength | 160° C. × 30 min | 120 | 111 | 109 | 104 | 123 |
| (kg/cm$^2$) | 160° C. × 40 min | 116 | 110 | 105 | 100 | 119 |
| Elongation | 160° C. × 20 min | 289 | 225 | 335 | 263 | 381 |
| (%) | 160° C. × 30 min | 243 | 182 | 211 | 204 | 305 |
| | 160° C. × 40 min | 194 | 149 | 194 | 168 | 205 |
| 100% | 160° C. × 20 min | 69 | 72 | 67 | 67 | 69 |
| Modulus | 160° C. × 30 min | 76 | 81 | 72 | 75 | 68 |
| (kg/cm$^2$) | 160° C. × 40 min | 83 | 86 | 74 | 79 | 79 |
| Hardness | 160° C. × 20 min | 84.5 | 81 | 82 | 83 | 83 |
| (JIS)* | 160° C. × 30 min | 86 | 82 | 84 | 84 | 84 |
| | 160° C. × 40 min | 86 | 83 | 84 | 84 | 85 |

*JIS: Japanese Industrial Standard

TABLE 24

| | No. | | |
|---|---|---|---|
| Compounds | 11 | 12 | 13 |
| Chlorinated polyethylene* | 100 | 100 | 100 |
| Carbon black (SRF) | 40 | 40 | 40 |
| Magnesium oxide | 10 | 10 | 10 |
| Di-isodecyl adipate** | 20 | 20 | 20 |
| Di-n-butylamine | 3.8 | 3.8 | 3.8 |
| Trithiocyanuric acid | 1.5 | 1.5 | 1.5 |
| DCBA[1] | — | 0.5 | 1.0 |
| Mooney Scorch Test - ML$_1$, 120° C. | | | |
| Minimum viscosity | 79.0 | 64.0 | 59.0 |
| t$_5$ (min, sec) | 4'00" | 5'55" | 7'00" |
| t$_{10}$ (min, sec) | 15'25" | 19'40" | 23'25" |
| t$_{\Delta 30}$ (min, sec) | 11'25" | 13'45" | 16'25" |
| Curastometer Test - 160° C. | | | |
| t$_{10}$ (min, sec) | 40" | 50" | 1'00" |
| t$_{90}$ (min, sec) | 25'50" | 26'35" | 24'50" |
| R (min, sec) | 25'10" | 25'45" | 23'50" |
| T (min, sec) | 51'00" | 52'20" | 48'40" |

*Vinycizer 401AE (Product of Showa Neoprene Co.)
**Elasten 50 (Product of Kao Sekken Co.)

Although the invention has been described with respect to particular compounds, methods of preparation of the compounds, and methods of use of the compounds, the invention is not limited to the particulars disclosed, but extends to all equivalent compounds, as well as to compounds falling within the scope of the invention but made or used in other ways than those specifically set forth. Likewise, the invention also extends to the compounds and their method of use, although the compounds may be made by a process different than that specifically disclosed.

What is claimed is:

1. The compound N-cyclohexylthio-N-cyclohexyl benzothiazole-2-sulfonamide.

2. The compound N-n-dodecylthio-N-cyclohexyl benzothiazole-2-sulfonamide.

3. The compound N-n-octylthio-N-cyclohexyl benzothiazole-2-sulfonamide.

* * * * *